United States Patent
Nathan et al.

(10) Patent No.: US 8,075,499 B2
(45) Date of Patent: Dec. 13, 2011

(54) ABNORMAL MOTION DETECTOR AND MONITOR

(75) Inventors: Vaidhi Nathan, San Jose, CA (US);
Chanden Gope, Cupertino, CA (US);
Anoo Nathan, San Jose, CA (US)

(73) Assignee: Vaidhi Nathan, San Jose, CA (US)

( * ) Notice: Subject to any disclaimer, the term of this patent is extended or adjusted under 35 U.S.C. 154(b) by 358 days.

(21) Appl. No.: 12/154,085

(22) Filed: May 19, 2008

(65) Prior Publication Data

US 2009/0062696 A1   Mar. 5, 2009

Related U.S. Application Data

(60) Provisional application No. 60/930,766, filed on May 18, 2007.

(51) Int. Cl.
*A61B 5/103* (2006.01)
*A61B 5/117* (2006.01)
(52) U.S. Cl. ........................................ 600/587; 600/595
(58) Field of Classification Search ............... 600/587, 600/595; 702/127, 141–154
See application file for complete search history.

(56) References Cited

U.S. PATENT DOCUMENTS

| | | | | |
|---|---|---|---|---|
| 5,916,181 A * | 6/1999 | Socci et al. | | 600/595 |
| 6,048,324 A * | 4/2000 | Socci et al. | | 600/595 |
| 6,730,047 B2 * | 5/2004 | Socci et al. | | 600/595 |
| 2002/0183657 A1 * | 12/2002 | Socci et al. | | 600/595 |
| 2004/0171969 A1 * | 9/2004 | Socci et al. | | 600/595 |
| 2004/0225236 A1 * | 11/2004 | Wheeler et al. | | 600/595 |

* cited by examiner

*Primary Examiner* — Jeffrey G Hoekstra
(74) *Attorney, Agent, or Firm* — David Lewis; Jayanthi Simha

(57) ABSTRACT

In an embodiment, a seizure monitor provides intelligent epilepsy seizure detection, monitoring, and alerting for epilepsy patients or people with seizures. In an embodiment, the seizure monitor may be a wearable, non-intrusive, passive monitoring device that does not require any insertion or ingestion into the human body. In an embodiment, the seizure monitor may include several output options for outputting the accelerometer/gyro or other motion sensor data and video data, so that the data may be immediately validated and/or remotely viewed. The device alerts and communicates to the outside care givers via wirelessly or wired medium. The device may also support recording of accelerometer or other motion sensor data and video data, which can be reviewed later for further analysis and/or diagnosis. The device and invention is also used and applicable for other body motion disorders or detection and diagnostics.

35 Claims, 12 Drawing Sheets

ABNORMAL MOTION DETECTOR AND MONITOR

CROSS-REFERENCE TO RELATED APPLICATIONS

This application claims priority benefit of U.S. Provisional Patent Application No. 60/930,766, entitled "Intelligent Seizure Detector and Monitor," filed May 18, 2007, by Vaidhi Nathan et al., which is incorporated herein by reference.

FIELD

This specification is related to medical devices.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Over two million people (about 1-3% of the population) suffer from epileptic seizures in the United States. During a seizure the patient is unable to get help, talk, think, or act. In many cases it is very important for doctors and caregivers to be able to detect seizures and give the patient immediate help. There are some types of seizures, if not attended to, that can be fatal. Currently there are no home or personal seizure monitoring or detecting devices. There are Electroencephalography (EEG) machines, which measure electrical activity in the brain. However, EEGs are for hospital use and are large and expensive. The EEGs may analyze brainwaves to detect the onset or the occurrence of a seizure. EEGs require probes to be mounted on the patients' scalp to sense, extract, and transmit data. The probes are uncomfortable, intrusive, and awkward—restricting patients movements and cause scarring. In addition, the graphs from the EEGs need to be reviewed and interpreted manually by trained personnel, such as nurses and medical assistants.

BRIEF DESCRIPTION

In the following drawings like reference numbers are used to refer to like elements. Although the following figures depict various examples of the invention, the invention is not limited to the examples depicted in the figures.

DETAILED DESCRIPTION

Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

In general, at the beginning of the discussion of each of FIGS. 1-3 is a brief description of each element, which may have no more than the name of each of the elements in the one of FIGS. 1-3 that is being discussed. After the brief description of each element, each element is further discussed in numerical order. In general, each of FIGS. 1-7 is discussed in numerical order and the elements within FIGS. 1-7 are also usually discussed in numerical order to facilitate easily locating the discussion of a particular element. Nonetheless, there is no one location where all of the information of any element of FIGS. 1-7 is necessarily located. Unique information about any particular element or any other aspect of any of FIGS. 1-7 may be found in, or implied by, any part of the specification.

In an embodiment, a seizure monitor provides intelligent epilepsy seizure detection, monitoring, and alerting for epilepsy patients and/or other people that experience seizures. In an embodiment, the seizure monitor is a small consumer usable device that is wearable and can be setup and used easily by patients. In an embodiment, the seizure monitor is compact and low cost. The seizure monitor may have at least any one of the following three different configurations or embodiments using—(i) motion sensor data (such as data from accelerometers, gyroscope sensors and/or other motion sensor data), or (ii) video data, and/or (iii) hybrid data (which may include both video and accelerometer or other motion sensor data). In an embodiment, the seizure monitor may be a wearable, non-intrusive, passive monitoring device that does not require any insertion or ingestion into the human body. In an embodiment, the seizure monitor may include several flexible and easy output options for outputting motion data, so that the data may be immediately validated and/or remotely viewed. The seizure monitor may also support recording of motion data that can be reviewed later by a medical professional for further analysis and/or diagnosis.

Seizure Detection System (FIGS. 1-3B)

Figure 1A:
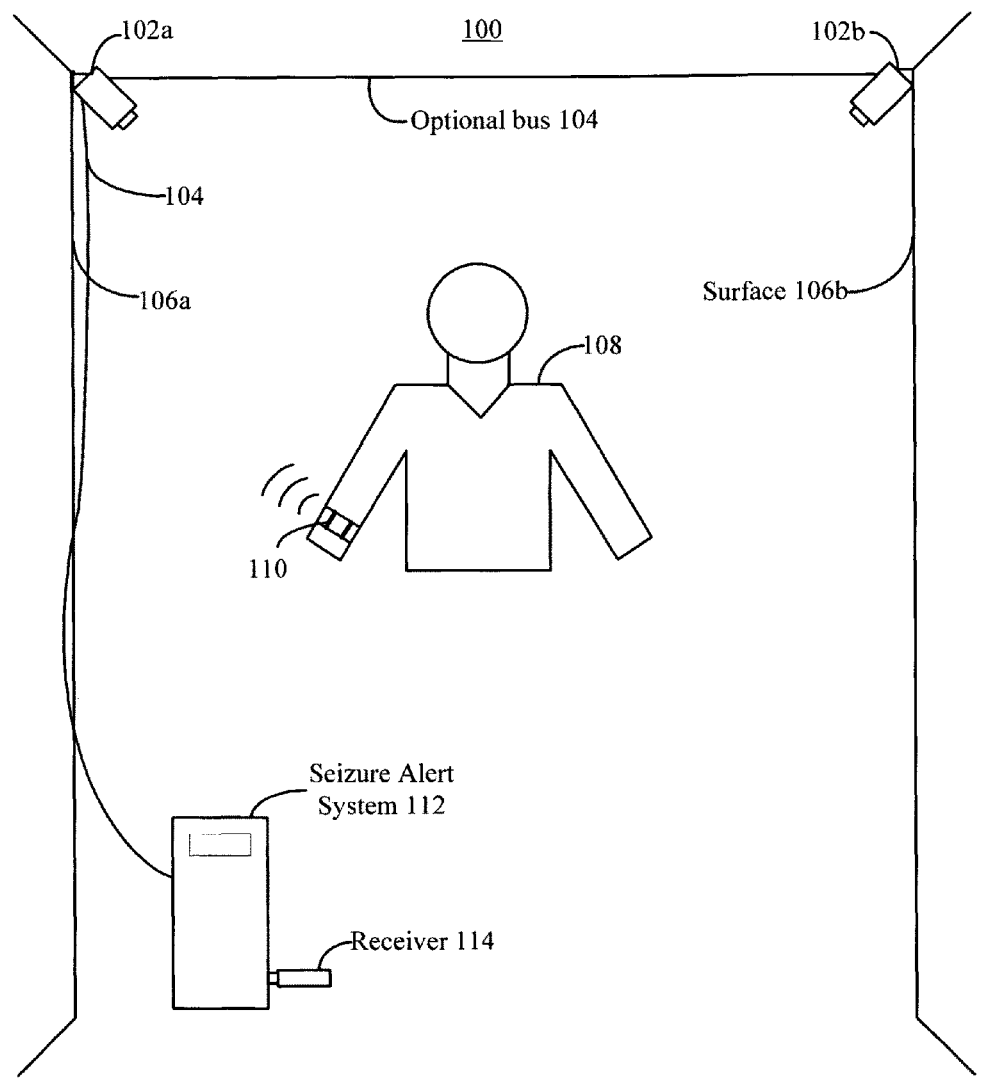
FIG. 1 shows a block diagram of an embodiment of seizure detection system 100.

FIG. 1A shows a block diagram of an embodiment of seizure detection system 100. Seizure detection system 100 may include cameras 102a-n, communications line 104, surfaces 106a-m, patient 108, motion detector 110, and receiver 112. In other embodiments, seizure detection system 100 may include additional components and/or may not include all of the components listed above.

Seizure detection system 100 may detect, monitor, and/or alert an concerned party of the onset and occurrence of epileptic seizures in patients. In this specification the term "concerned party" includes any entity or person that may have an interest in knowing about the occurrence of a seizure, such as caregiver, medical professional, close friend, or relative of the patient. In an embodiment, seizure detection system 100 may be passive, compact, and/or non-intrusive.

Although throughout the specification seizure detection system 100 is discussed, seizure detection is just one example of a motion disorder that may be detected with seizure detection system 100. Although the discussion of this specification focuses on seizure monitoring and detection, there are other motion based diagnostics or body motion analysis that may be performed using the same system.

Each analysis can be different. But the HW can use the same. Just the rules or conditions or pattern recognition can be different.

Cameras 102a-n may include any number of cameras, which film a patient in order to capture on film images that may be analyzed to determine whether a seizure is in progress. As also elaborated upon elsewhere, cameras 102a-n are optional. Cameras 102a-n are optional, and may be replaced with another form of detecting seizures, such as motion detectors. For example, another type of motion detector, such as infrared detectors, may be used instead of, or in addition to, cameras 102a-n. Although cameras 102a-n are illustrated as being mounted on surfaces within a premise of the patient, cameras 102a-n may be mounted on the patient, and instead of observing the patient to determine the motion of the patient, the motion of patent may be inferred from the images of the surroundings of the patient, for example.

Optical sensors, such as video camera 102a-n can be used to monitor the patient and detect seizure-like activities. Seizure-like activities may offer unique motion patterns and can be distinguished from non-seizure-like activities. Easily distinguishable feature points (or feature points corresponding to particular body parts that are significant in determining whether or not a seizure is in progress) in the scene can be computed (such as those on the person or an object) and the temporal motion patterns of the feature points (such as points on the person's body or clothes) can be analyzed across frames for detection of any abnormal activity. Some motion patterns of interest could be large movements in short periods of time, repetitive movements, back-and-forth movements, etc. Further, some special seizure activities offer very characteristic and predictable motion patterns, a prior knowledge of which can be utilized effectively to detect such cases.

Communications line 104 communicatively connects cameras 102a-n to a processor (for analyzing the motion data and determining whether a seizure is occurring) and/or seizure alert system. In an embodiment, instead of or in addition to communications line 104, cameras 102a-n may communicate wirelessly with a processor and/or seizure alert system.

Surfaces 106a-m support cameras 102a-n. Patient 108 suffers from seizure and is monitored by the rest of seizure detection system 108 to determine whether a seizure has occurred. In this specification the word "patient" refers to any individual that is being monitored to determine whether a seizure is occurring.

Motion detector 110 is mounted on patient 108 so that motions of the patient may be measured. In an embodiment, motion detector 110 is an accelerometer, a gyro sensor, and/or a hybrid of both. Motion detector 110 communicates wirelessly (or via wires) with a seizure alert system. Motion detector 110 may include a transmitter for transmitting information about motion measured by motion detector 110. Optionally, motion detector 110 may include a location determining unit (e.g., a global positioning unit) for determining the location of patient 108 and transmitting the location of the patient 108 to a concerned party. In an embodiment there are multiple motion detectors 110 mounted on patient 108. In another embodiment, there is only one motion detector 110 mounted on patient 110. If motion detector 110 is a small accelerometer (and/or gyro sensor), no other element needs to be worn or placed on patient 108, and the accelerometer (and/or gyro sensor) may be passive and non-intrusive. Although often in this specification an accelerometer and/or gyro are referred to another motion sensor(s) may be used instead. The detection of the seizure or movement patterns can be done inside the watch itself. The results and/or an alert may be sent outside via wireless or wired medium. Alternatively, the watch can simply send only the sensor data, and the detection and decision can be made outside on the phone or a computer outside the watch sensor. Both options are viable.

One way of detecting seizures is to monitor the motion of one or more parts of the body of patient 108. During a seizure there are rapid and jerky movements of one or more body parts, such as the hands, legs, torso, and head. Seizures can be detected by measuring the change in output of a motion detector, the frequency of the change, and/or amplitude of the change indicating a movement of one or more body parts.

There are different types of motion detectors, which may be used of motion detector 110. One type of motion detector is an accelerometer, which measures acceleration. Ordinarily, when stationary, each part of the body experiences the acceleration of gravity (an accelerometer cannot tell the difference between a body being accelerated as a result of the body's changes in velocity and the body being pulled by a force, such as gravity). From the changes in acceleration, changes in position and/or velocity may be inferred. When a body part moves, the acceleration of the body part changes, and thus the change in the acceleration indicates a motion. Another type of sensor data is gyro sensor data. Gyro sensors may detect the rotation along X, Y, and/or Z axes. The rotation angles and position can also be used to detect motion and particular types of motion. While accelerometer measures linear axis changes, gyros measure the rotation changes.

The sensor that is used as motion detector 110 may a small device that can fit into an enclosure the size of a wristwatch. The motion data may be measured in two-dimensions (e.g., along two perpendicular axes, which may be referred to as the X and Y axes) and/or three-dimensions (e.g., along three perpendicular axes, which may be referred to as the X, Y, and Z axes). Acceleration, frequency, and amplitude (angle, angular velocity, angular acceleration, and angular impulse or jerk) values above a certain threshold are indicative of abnormal body movements that occur during a seizure. If two two-dimensional (X,Y) motion sensors are used as motion detector 110, each of the two-dimensional (X,Y) motion sensors may be paced along perpendicular axes. The two-dimensional and/or three-dimensional motion sensors can be useful to detect the jerky and back and forth movements. The detection algorithm is discussed below. Motion detector 110 can be positioned and/or mounted on the patient's arms, legs, bedclothes, and/or the bed itself. Motion detector 110 placed on the patient's body may be more effective and accurate in detecting seizures.

Seizure alert system 112 alerts a concerned party when a seizure occurs. Seizure alert system 112 may be a PC, laptop, PDA, mobile phone bell, and/or other unit capable of indicating an alert. Information in signals from cameras 102a-n and/or motion detector 110 are analyzed, and if it is determined that a seizure is occurring, an alert is output from alert system 112. Seizure alert system 112 may include a monitor for displaying seizure alerts and/or for displaying motion data. In an embodiment, seizure alert system 112 may include a processor for analyzing the signals from cameras 102*a-n* and/or motion detector 110. In an embodiment, system 100 is a general purpose alerting system and can also alert other motion disorders.

Motion sensors that are included within motion detector 110 may be attached to the wrist explicitly capture the motion along the x, y, and z directions. The data obtained may be a time sequence of the instantaneous acceleration experienced by the sensor. Several approaches can be used here to detect any abnormal seizure-like activities. These approaches can be divided broadly into two categories:

In an embodiment, a processor, which may be located in seizure alert system 112 or elsewhere may run algorithms to determine whether a seizure is occurring, and when it is determined that a seizure is occurring alerts may be output from seizure alert system 112. In an embodiment, along with the alerts, one or more confirmation images and/or accelerometer or other motion sensor plots may also be sent to a concerned party, such as a doctor and/or other caregiver. The alert may be sent, via SMS, MMS, email, IM, or WAP or other message protocol. The alert may include an alert message, alarm signal, beeps, local in-device sound alerts, and/or alarms, which may be produced by a PDA, mobile phone, or other device, which may have built in alarms and alerts.

Receiver 114 receives signals from transmitters on wireless units such as motion detectors 110. Receiver 114 is optional. If cameras 102*a-n* do not communicate via communications line 104 (e.g., if communications line 104, is not present), receiver 114 may receive signals from cameras 102*a-n*. Thus, depending on the embodiment, seizure detection system 100 may detect motion via video data from cameras 102*a-n*, sensor data from motion detector 110, and/or hybrid data (which is data based on both cameras 102*a-n* and/or sensor data from motion 110).

One example of an embodiment encompassed within FIG. 1 may include input sensors (video and/or motion sensors, such as accelerometers), one or more computers for receiving and processing data from the sensors, connectivity interfaces, and a system for remotely monitoring and for alerting (e.g., sending an alarm) a concerned party. The connectivity interface may include any of a number of communications interfaces, such as Bluetooth interfaces and/or Wifi, wireless interfaces, and/or wired interfaces, which may use IP/LAN connections and/or serial port connections, such as USB.

Another example of an embodiment encompassed within FIG. 1 may be a video based system, which may include one or more cameras (such as analog cameras, WebCam cameras, and/or IP/Network cameras) and/or IR detectors and/or illuminators for nighttime monitoring and analysis. The cameras may be color or infrared cameras, for example. The cameras can be connected to the a Personal Computer (PC) and/or any computing device, via (i) a wireless interface, such as a WIFI/LAN interface, a Serial/USB wireless interface, and/or BlueTooth interface, and/or (ii) a wired interface such as a LAN and/or Ethernet interface. Video data is received by the computing device analyzed and/or processed. The results of the analysis and/or processing are transmitted to the concerned party. Alternatively, processing intelligence, an analysis engine, and/or algorithms that reside in the computing device may be embedded and/or otherwise built into the camera resulting in a "Smart Camera." In an embodiment, there may be a camera and optional IR illuminators for nighttime monitoring and analysis, and there may not be an accelerometer. There may be a processor that executes the algorithm, and processor may be located inside or outside of the camera. Detection as a result of analyzing the motion data may occur within the processor in the camera or in a processor located elsewhere. Alerts may be communicated via an external media to a concerned party.

In a video based embodiment, the input data to the processor may be a stream of video data from the camera. The camera may be connected to a PC or other computing device, such as a PDA or smart mobile phone. The camera may also have an intelligent processor embedded inside, that processes and analyzes the input data.

In a film based seizure detection system, alerts and other output may communicate via alarms, SMS, MMS, IM, WAP message, email, or a phone call to the concerned part. Alerts may be sent either over a LAN (a wired network), a wireless network, or over a GSM/cellular mobile network.

Another example of an embodiment encompassed within FIG. 1 may be an accelerometer (and/or a gyro sensor) based system, which may include an accelerometer (as a motion sensor). The accelerometers may provide two-dimensional and/or three-dimensional data related to one or more axes of acceleration, rotation, and/or velocity, if available. The accelerometer may be communicatively connected to the rest of seizure detection system 100 by a Wired/LAN interface, Wireless/BlueTooth/Zigbee/Wifi interface, and/or Serial/USB interface. The processor that processes the motion data may be located within an external PC or other device, such as a smart mobile phone or other handheld device.

In an embodiment, there may be a motion sensor (an accelerometer or gyro sensor) without any video camera, which is simpler and cheaper. There may be a processor that operates the algorithm, and processor may be located inside or outside of the motion sensor. In other words, detection may be performed via an algorithm executing within the processor to determine if a particular motion is a seizure. Alerts may be communicated from the processor via external any of a number of media to a concerned party.

In the embodiment that is based on a motion sensor, the input data may be a stream of analog or digital signals or values from the accelerometer/gyro sensor. The accelerometer or other motion sensor may have a built in processor to interpret and process the input data. Alternatively the accelerometer or other motion sensor may be connected to a PC or other computing device, such as a smart mobile phone or PDA. The processor may execute seizure detection algorithms.

In the embodiment, that in which an accelerometer is the motion detector 110, alerts and other output may be communicated via alarms, SMS, WAP messages, email, or phone calls to the people specified. Alerts may be sent either over LAN (wired) or wirelessly or over the GSM/cellular mobile networks.

In an embodiment, both video camera and accelerometer/gyro sensor may be used to determine whether there is a seizure. This embodiment may include features and elements of both video and accelerometer/gyro sensor systems, mentioned above. Both detectors may run in parallel. Images from the video system may be used for additional confirmation and validation of the data from the accelerometer systems. These systems may run 24 hours per day, seven days a week, 365 days per year, all the time, or on an as-needed basis. The seizure detection system 100, seizure alert system 112, cameras 102*a-n*, motion detector 11 may be powered externally or may be powered by a battery. In an embodiment, there may be multiple levels or thresholds. For example there may be two levels or thresholds each indicating a different degree of danger or indicating a different degree of certainty that a seizure occurred. In some cases, there may be a threshold for even suspected conditions may be recorded. In one embodiment, one threshold or level may indicate that there is a problem that is observed, which may record the event or condition without actually activating an alert and at a second level or threshold an alert may be activated. Activating the alert may include sending a communication indicating the alert. In an embodiment, alerts are sent for only conditions or seizures that pass certain conditions or levels. In an embodiment, there may be a button to indicate that there is a seizure occurring now, which may include an ask-for-help button. In an embodiment, the patient may be able to manually trigger the alert to be activated. In an embodiment, if the system detects a problem, but the patient is fine, the patient can press a button and indicate to ignore the alarm and that the call this false alarm. These thresholds can be adjusted by the patient/user. Each user may have different threshold or personal requirement on when to record and when to alert. The system may provide two adjustable sets of thresholds that can be modified. One set of thresholds is for sending an alert and one set of thresholds is for recording events that have seizure-like characteristics, but are expected not to be a seizure or for events that are near the borderline between being a seizure and not being a seizure. The input parameters may be entered manually by the user, stored, and reused, so that the user not need to input the parameters every time system 100 is turned on or put in use.

In this approach, we utilize the input signal as is. The data can be windowed (overlapping) over short durations of time and the range of values examined. It is expected that non-seizure-like activities exhibit value fluctuations only within a short range of values of acceleration (or gyro sensor), that is, the difference between the minimum acceleration value and the maximum acceleration value over a short period of time is bounded by two relatively close values. On the other hand, seizure-like activities exhibit a larger fluctuation and the difference between the minimum acceleration value and the maximum acceleration value.

There at least are four strategies to implement the detection system. Any one of these four strategies is sufficient and can be used to do the detection (1) learning based and/or (2) rules, conditions and/or logic based, (3) probabilistic/statistical models and detection methods and (4) analysis of local, regional, global features which include both data and temporal information. A hybrid of any combination these four strategies can also be used. Seizure detection system 100 may be based on learning system and incorporate supervised or unsupervised learning, which may include one or more neural-networks, machines that perform pattern recognition methods and/or support vector machines, for example. In embodiments including unsupervised learning, positive and negative data samples are provided to seizure detection system 100 as training examples for classifying patterns of behavior as seizure or non-seizure motion patterns. After being fed the training examples, seizure detections system 100 is able to make a determination as to whether other motion patterns are associated with seizures. By using unsupervised learning, after a training session and/or after learning from experience with actual motion patterns of patient 108, seizure detection system 100 is able to detect seizures having motion patterns that do not have features that are otherwise common amongst most other seizure-like activities. For example, a neural-network or a Support Vector Machine can be trained based on positive and negative data samples.

Alternatively, the detection system or algorithm can be based on rules, conditions, or equations and pre-defined logic that is patient independent. For example, the rule or logic can be to compute the local peaks of motion jerks. If there are N jerks happen within M seconds, then the motion may be determined to be seizure. For example, if # jerks are >5 within 3 secs, then it is a seizure. Typical rules/logic will use one or more conditions or criteria based on: frequency/number of motion/jerks within a time frame, amplitude of the motion, continued change or duration of this motion, $1^{st}$ or $2^{nd}$ degree change of these values above. These rules/logic/conditions will change between the type of seizures like TonicClonic, Partial or Complex Seizures etc. Caregivers or patients can also adjust these rules/conditions/thresholds, to better suit their individual needs and type of seizures. There can also be defined set of types of conditions or detection rules templates, built in and users can select and chose and test different ones and pick the ones they like most.

In an embodiment, the motion data from cameras 102a-n and/or from motion detector 110 is transformed into the frequency domain, via a Fourier transform, or wavelet transform. In the frequency domain, the motion data is analyzed to see whether the motion data includes unique features in the frequency domain (such as larger coefficients corresponding to high frequency components) that are expected to be found in motion data from a seizure. Performing a Fourier transform on a set of data taken within a particular window of time may be taken, (which may be referred to as a "windowed Fourier transform" and) which may capture the local nature of the signal. Similarly, orthogonal wavelet transforms (such as Daubechies) or another transform of the motion data may be taken (which may also provide a local representation of the signal in terms of the set of basis functions). The transformed may then be scanned for large coefficients of basis vectors that are expected to be associated with a seizure. The recognition seizure motion patterns in the frequency domain may be performed based on a supervised or unsupervised learning.

In an embodiment there may be a bank of motion detectors, which may include any combination of cameras 102a-n, motion detector 110, other hybrid motion detectors, and/or other motion detectors, as described above, each running in parallel. The usage of a bank of motion detectors creates a system that is very robust and that detects seizures with a high level of accuracy.

In an embodiment, an accelerometer in a watch measures the accelerations in the three directions, $a_x$, $a_y$, and $a_z$. Optionally, from the individual components that magnitude can be computed from $a=SQRT(a_x^2+a_y^2+a_z^2)$. Optionally, the magnitude may be used to compute the absolute first derivative of the acceleration $v=|a_n-a_{n-1}|$, which is equivalent to "jerk." Optionally, the absolute second derivative may be computed $v'=|a_n-2a_{n-1}+a_{n-2}|$. The first and/or second derivative of each component may be computed and/or the first and/or second derivative of magnitude may be computed. In an embodiment, a count is performed of all of the peaks of the first and/or second derivative that occur during a specified time window that are above a certain threshold. If the number of peaks is greater than a threshold number, it is assumed that a seizure is occurring.

If a preset number of peaks in the amplitude of the acceleration are obtained within a certain time interval, then it is considered to be a seizure. If less than the preset number of peaks in the amplitude of the acceleration are obtained within the time interval, then it is assumed that a seizure did not occur. In an embodiment, the variation of each component of acceleration is analyzed separately (in addition to or instead of analyzing the magnitude of the acceleration). During a seizure, in each component of the acceleration, the peaks may be more frequent and shorter than for the amplitude, and consequently, for each component of acceleration, the threshold for the number of peaks (that is considered indicative of a seizure) in a given time period may be set higher and the threshold for the amplitude of the peaks (that is considered indicative of a seizure) may be set lower than for the magnitude. The positive and negative examples of motion patterns that are fed to a neural network or other learning algorithm may include each component of acceleration and/or the magnitude of the acceleration.

Figure 1B:
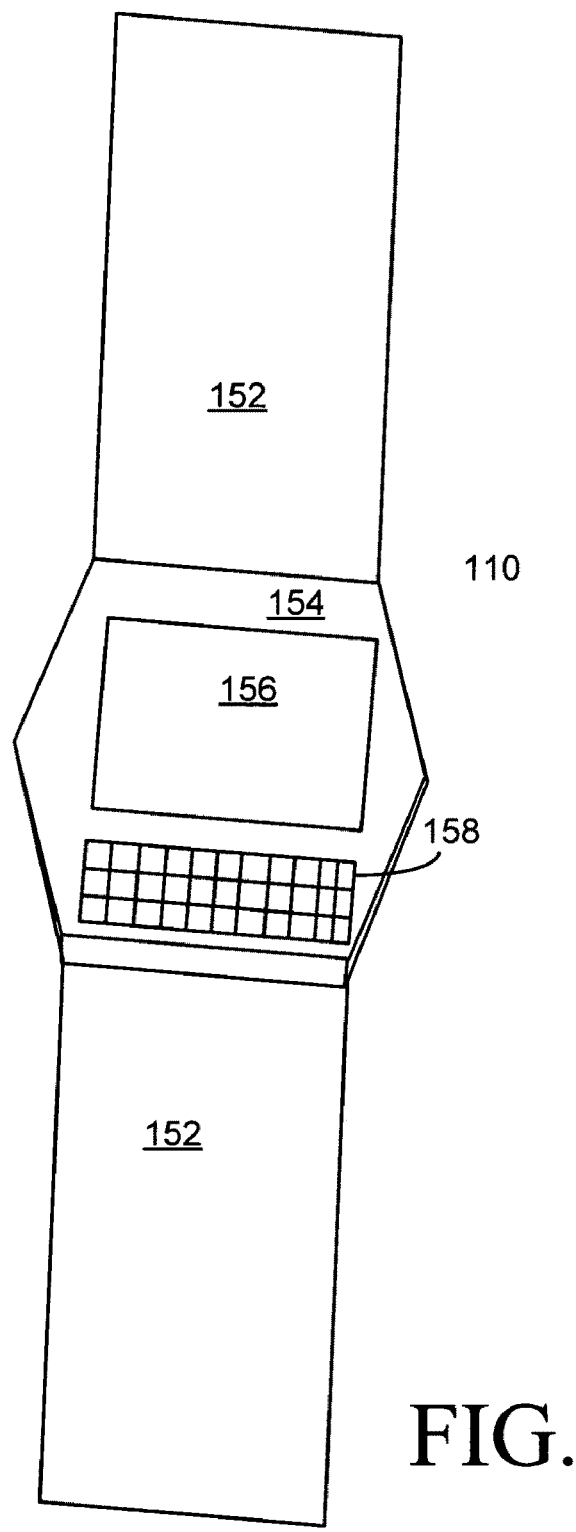

FIG. 1B shows a representation an embodiment of seizure detection system 150. Seizure detection system 150 band 152, housing 154, display 156, and input interface 158. In other embodiments, seizure detection system 150 may include additional components and/or may not include all of the components listed above.

Seizure detection system 150 is an embodiment of a seizure detection system that is a device that is also a wristwatch, that is within a device that is a wristwatch, or doubles as a wrist watch. Other embodiments of seizure detection system 150 may be worn elsewhere on an arm, on a hand, on a leg, on a foot, on a chest, and/or other part of a person. Seizure detection system 150 may include a motion detector (not shown in FIG. 1B), such as an accelerometer, for motion detector 110 (FIG. 1A). Band 152 may be used for fastening seizure detection system 150 to a wrist of patient 108 (FIG. 1A). Housing 154 contains the circuitry for seizure detection system 100 (FIG. 1A). Display 156 may display settings of seizure detection system 150, the time, and/or output of seizure detection 156. Input interface 158 may be a series of buttons for inputting settings for seizure detection system 150 and/or for inputting wristwatch settings.

Figure 2A:
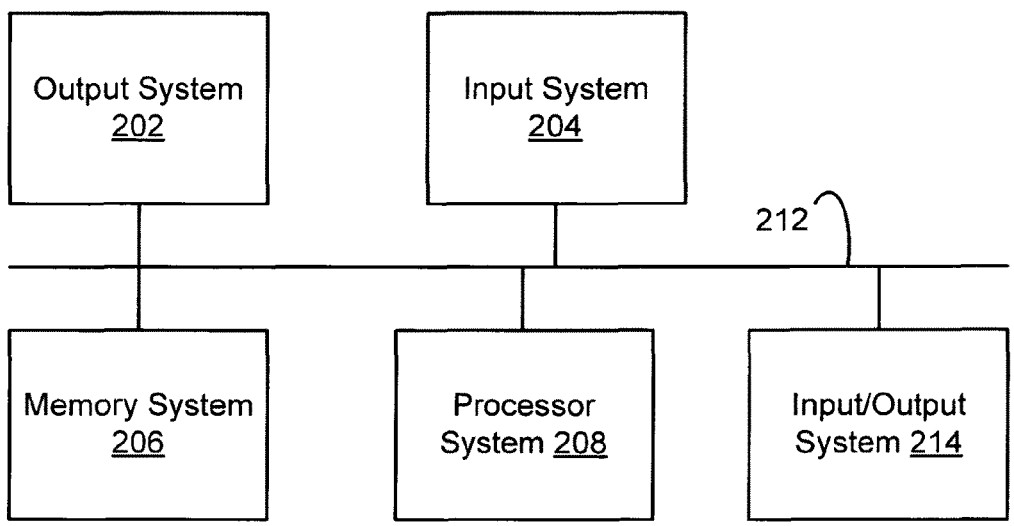
FIG. 2A shows a block diagram of system 200, which may be incorporated within the system of FIG. 1.

FIG. 2A shows a block diagram of system 200, which may be incorporated within the system of FIG. 1. System 200 may include output system 202, input system 204, memory system 206, processor system 208, communications system 212, and input/output device 214. In other embodiments, system 200 may include additional components and/or may not include all of the components listed above.

System 200 may be an embodiment of seizure detection system 100 in which seizure detection system 200 is contained within one unit. Alternatively or additionally, an embodiment of seizure detector 112 may be system 200. Output system 202 may include any one of, some of, any combination of, or all of a monitor system, a handheld display system, a printer system, a speaker system, a connection or interface system to a sound system, an interface system to peripheral devices and/or a connection and/or interface system to a computer system, intranet, and/or internet, for example. Output system 202 may include lights, such as a red light and/or a flashing light to indicate a seizure. Output system may include sounds such as beeps, rings, buzzes, sirens, a voice message, and/or other noises. Output system 202 or a part of output system 202 may be kept in the possession of a care taker or in a location that will catch a care taker's attention, such as a PDA, cell phone, and/or a monitor of a computer that is viewed by a care taker. Output system 202 may send an e-mail, make a phone call, and/or send other forms of messages to alert a concerned party about the occurrence of a seizure.

Input system 204 may include any one of, some of, any combination of, or all of a keyboard system, a mouse system, a track ball system, a track pad system, buttons on a handheld system, a scanner system, a microphone system, a connection to a sound system, and/or a connection and/or interface system to a computer system, intranet, and/or internet (e.g., IrDA, USB), for example. Input system 204 may include a motion detector and/or camera for detecting high frequency motion. Input system 204 or a part of input system 204 may be kept in the possession of a care taker or in a location easily accessible to a concerned party so that the concerned party may request current motion information and/or past motion and/or seizure information. For example, input system 204 may include an interface for receiving messages from a PDA or cell phone or may include a PDA and/or cell phone.

Memory system 206 may include, for example, any one of, some of, any combination of, or all of a long term storage system, such as a hard drive; a short term storage system, such as random access memory; a removable storage system, such as a floppy drive or a removable drive; and/or flash memory. Memory system 206 may include one or more machine-readable mediums that may store a variety of different types of information. The term machine-readable medium is used to refer to any medium capable carrying information that is readable by a machine. One example of a machine-readable medium is a computer-readable medium. Another example of a machine-readable medium is paper having holes that are detected that trigger different mechanical, electrical, and/or logic responses. Memory system 206 may store seizure detection engine and/or information about seizures. Memory system 206 will be discussed further in conjunction with FIG. 2B. If system 200 is seizure alert system 112, memory system 206 is optional, because the processing and storage of seizure information may occur elsewhere.

Processor system 208 may include any one of, some of, any combination of, or all of multiple parallel processors, a single processor, a system of processors having one or more central processors and/or one or more specialized processors dedicated to specific tasks. Processor system 208 may run a program stored on memory system 206 for detecting seizures, which may be referred to as a seizure detection engine. Processor system 208 may implement the algorithm of seizure detection system 200. Processor system 208 may collect the data from one or more accelerometers and/or video sensors. Processor system 208 may implement a detection and analysis algorithm on the data. If system 200 is an embodiment of seizure alert system 112, processor system 208 is optional, because the processor may be located elsewhere.

As a digression, if seizure detection system 112 is not one unit, the processor system may be located at one of at least four locations, which include within an external device such as a PC or laptop, within a handheld device, within a camera, within an accelerometer. Data may be streamed to the external device via a wired connection (such as LAN/USB/Serial) and/or a wireless connection (such as Wifi/BT). The handheld computing device may be a PDA, mobile phone, or other handheld device. In other words, the detection engine and algorithm may reside inside the handheld device. The data may be streamed to the mobile phone or hand-held/PDA, and the processing and/or analysis may be executed on the handheld device. The processor of seizure detection system 100 may be located and built into any one of or any combination of cameras 102a-n. In other words, the processor with the detection engine (the software that analyzes the sensor data to determine whether a seizure occurred) may be embedded inside of any one of or any combination of camera 102a-n and the detection processing may be carried out inside the camera. In an embodiment, processor system 208 may be located within a handheld device, which may be an embodiment of seizure alert system 112 and/or seizure detection system 100 may be a handheld device strapped to patient 108 (FIG. 1) in which processor 208 is located.

Communications system 212 communicatively links output system 202, input system 204, memory system 206, processor system 208, and/or input/output system 214 to each other. Communications system 212 may include any one of, some of, any combination of, or all of electrical cables, fiber optic cables, and/or means of sending signals through air or water (e.g. wireless communications), or the like. Some examples of means of sending signals through air and/or water include systems for transmitting electromagnetic waves such as infrared and/or radio waves and/or systems for sending sound waves.

Input/output system 214 may include devices that have the dual function as input and output devices. For example, input/output system 214 may include one or more touch sensitive screens, which display an image and therefore are an output device and accept input when the screens are pressed by a finger or stylus, for example. The touch sensitive screens may be sensitive to heat and/or pressure. One or more of the input/output devices may be sensitive to a voltage or current produced by a stylus, for example. Input/output system 214 is optional, and may be used in addition to or in place of output system 202 and/or input device 204.

Figure 2B:
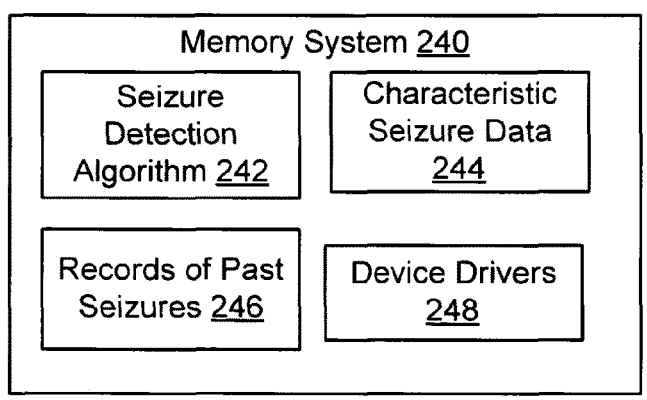
FIG. 2B shows a block diagram of an embodiment of memory system 206.

FIG. 2B shows a block diagram of an embodiment of memory system 206. Memory system 206 may include seizure detection algorithm 242, characteristic seizure data 244, records on past seizures 246, and device drivers 248. In other embodiments, memory system 206 may include additional components and/or may not include all of the components listed above.

Seizure detection algorithm 242 analyzes motion data to determine whether a seizure has occurred. Characteristic seizure data 244 includes information characterizing a seizure. Characteristic seizure data 244 may include thresholds for various parameters that are indicative of a seizure having taken place. For example, characteristic seizure data may include one or more thresholds for the frequency of oscillation of a various body parts during a seizure, thresholds for frequency of oscillation of the acceleration or other parameter output by the accelerometer and/or a threshold of the frequency of oscillation of cantilever that is part of the an accelerometer that is included within motion detector 110. Characteristic seizure data 244 may include patterns of data that are indicative of a seizure. Characteristic seizure data 244 may include default data that is not specific to any one individual and/or may include data that is specific to patient 108.

Records of past seizures 246 may store information about seizures as the seizures are happening, which may be reviewed further by at a later date to better determine the characteristics of the seizures that are specific to patient 108 so that seizure detection system 100 may more reliably detect the seizures of patient 108. Additionally or alternatively, records of past seizures 246 may be used for diagnosing and treating the seizure. In an embodiment, all detection results may be recorded on the hard disk of a PC or on an external memory card (SD, Compact Flash, Memstick etc). In some instances, knowledge of whether a seizure occurred may be important to know the effectiveness of a medication or for other medical reasons. However, some patients are unaware of having experienced a seizure. By storing records of past seizures 246, patient 108 may nonetheless be informed that a seizure was experienced. The data may include images, videos, accelerometer, or other motion sensor data. The data may include plots, summaries and/or other forms of data. The data may be analyzed and reviewed later by a medical professional for diagnosis and/or other medical purposes. Device drivers 248 include software for interfacing and/or controlling the motion detector.

Figure 3A:
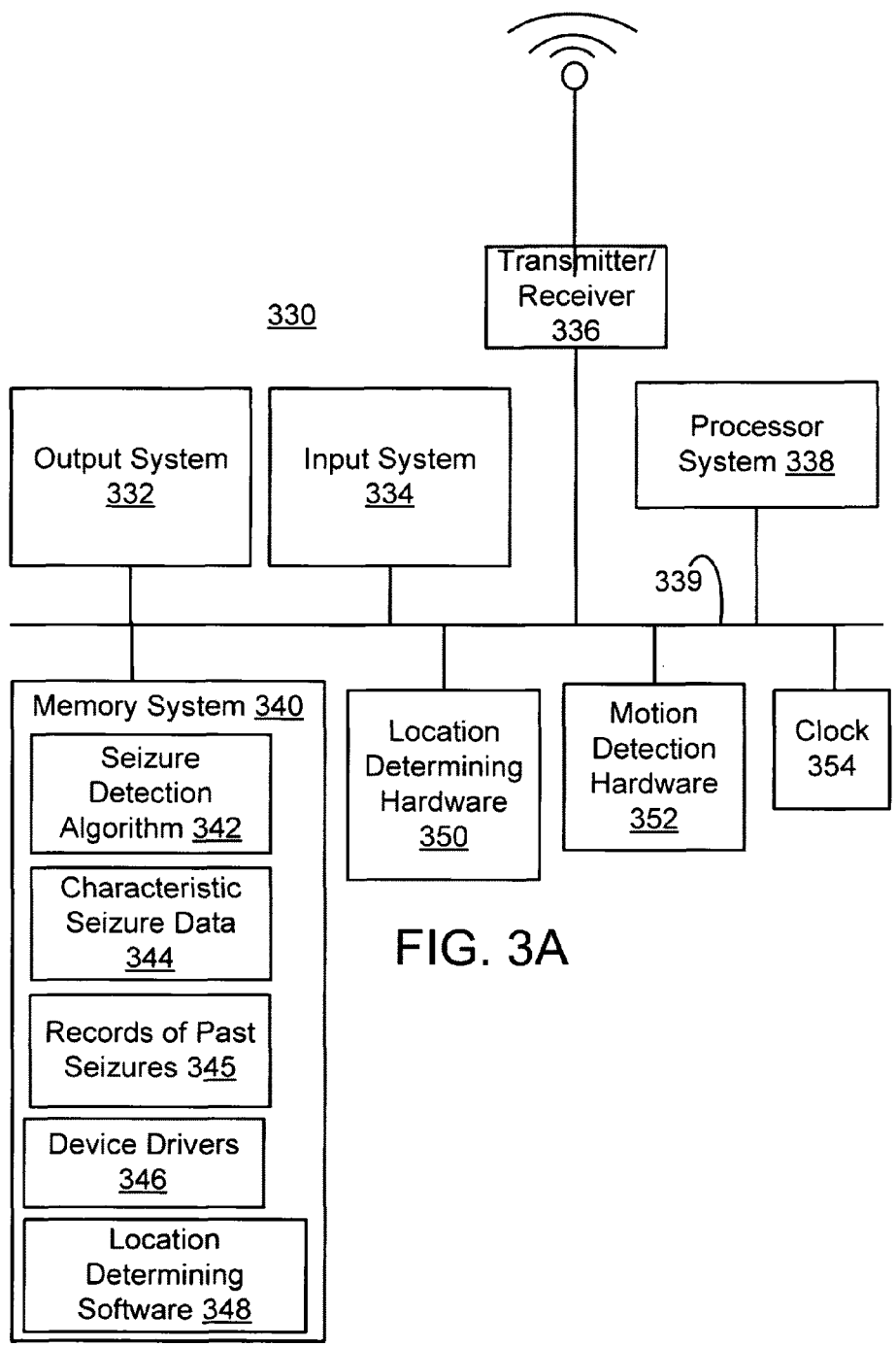
FIG. 3A shows a block diagram of an embodiment of motion detector 110.

Motion Detector with Processor (FIG. 3a)

FIG. 3A shows a block diagram of an embodiment of motion detector 110. Motion detector 110 may include output system 332, input system 334, transmitter/receiver 336, processor system 338, communications system 339, memory system 340, which may include seizure detection algorithm 342, characteristic seizure data 344, records of past seizures 345, device drivers 346, and/or location determining software 348. Motion detector 110 may also include location determining hardware 350, motion detection hardware 352 and clock 354. In other embodiments, motion detector 110 may include additional components and/or may not include all of the components listed above.

Output system 332 is optional and may include a display for providing feedback regarding whether various settings are set and/or may provide the values of the current settings. Input system 334 is optional and may include buttons and/or a pad for entering user settings. Optionally, output system 332 and input system 334 may include an interface for communications line 104 to seizure alert system 112. Receiver/transmitter 336 may include an antenna, other hardware, and/or software for communicating wirelessly with other devices, such as seizure alert system 112 (e.g., via receiver 114).

Processor system 338 may be any one of, some of, any combination of, or all of multiple parallel processors, a single processor, a system of processors having one or more central processors and/or one or more specialized processors dedicated to specific tasks. Processor system 338 may run a program stored on memory system for detecting seizures, which may be referred to as a seizure detection engine, and/or may perform other functions. Communications line 339 may be a bus that allows the various components of motion detector 110 to communicate with one another.

Memory system 340 may include programs for running motion detector 110 and for interfacing with other equipment. Seizure detection algorithm 342, characteristic seizure data 344, records of past seizures 345, device drivers 346 have essentially the same description as seizure detection algorithm 242, characteristic seizure data 244, records on past seizures 246, and device drivers 248 (FIG. 2B), respectively. Location determining software 348 is optional and includes software for determining the location of the patient 108 for situations in which patient 108 is having a seizure in an otherwise unknown location. For example, location determining software 348 and location determining hardware 350 may be global positioning software and hardware (for a GPS system), respectively. Location determining software 348 and location determining hardware 350 are optional and if location determining software 348 and location determining hardware 350 are global positioning software and hardware, location determining hardware 350 may process signals from, and/or communicating with, location determining satellites to produce the location determining data that is further processed by location determining software 348. Motion detection hardware 352 is the hardware that detects the motion of patient 108 (FIG. 1). Motion detection hardware 352 may include an accelerometer, which may include a cantilever with a weight attached to one end and a circuit for detecting deflections of the cantilever.

In an embodiment, the seizure detector may be included within a watch, hand strap, leg strap, and/or strapped to another part of the body. For example, an accelerometer/gyro sensor coupled with Bluetooth/Zigbee wireless (or USB or LAN) connectivity may be included in the watch, hand strap, and/or leg strap for detecting seizures. One or more processors may be attached to an arm coupled to the accelerometer or other motion sensor and/or incorporated within or attached to a mobile phone. In an embodiment, watch and the mobile phone in combination may provide a complete system that records and analyzes data related to possible seizures. Based on the analysis, there may be a detection of a condition that is expected to be a seizure, and an alert and/or other output communication may be sent.

Hand-Worn "Seizure Detection" Watch

In an embodiment, seizure detection system 100 or motion detector 110 may be a seizure detection watch, worn by a patient, for example. The seizure detection watch may contain a wireless transmitter (using Bluetooth/Zigbee/Wifi/RF), an accelerometer or other motion sensor, a battery, and a processor. The sensor detects motion and generates signals that correspond to the motion. The processor processes the signals using a detection algorithm that analyzes the signals and determines (and thereby detects) whether a seizure occurred. As described in conjunction with FIG. 1, the Bluetooth transmitter sends the seizure detection to the outside world via the Bluetooth, SMS, MMS, WAP, or email, IM, IP messages to another device (which may be a mobile phone, PC, Laptop, or PDA). In an embodiment, the "smart watch" is an intelligent "seizure detector" device that may do some/all the detection and alerting. In addition the Watch, can also have some LED lights and/or buzzer to indicate the status of detection and what the system thinks and decides. Hence patients can look at the LEDs or hear the sound and understand the status. There may or may not be any visual displays, besides these lights and sounds.

Figure 3B:
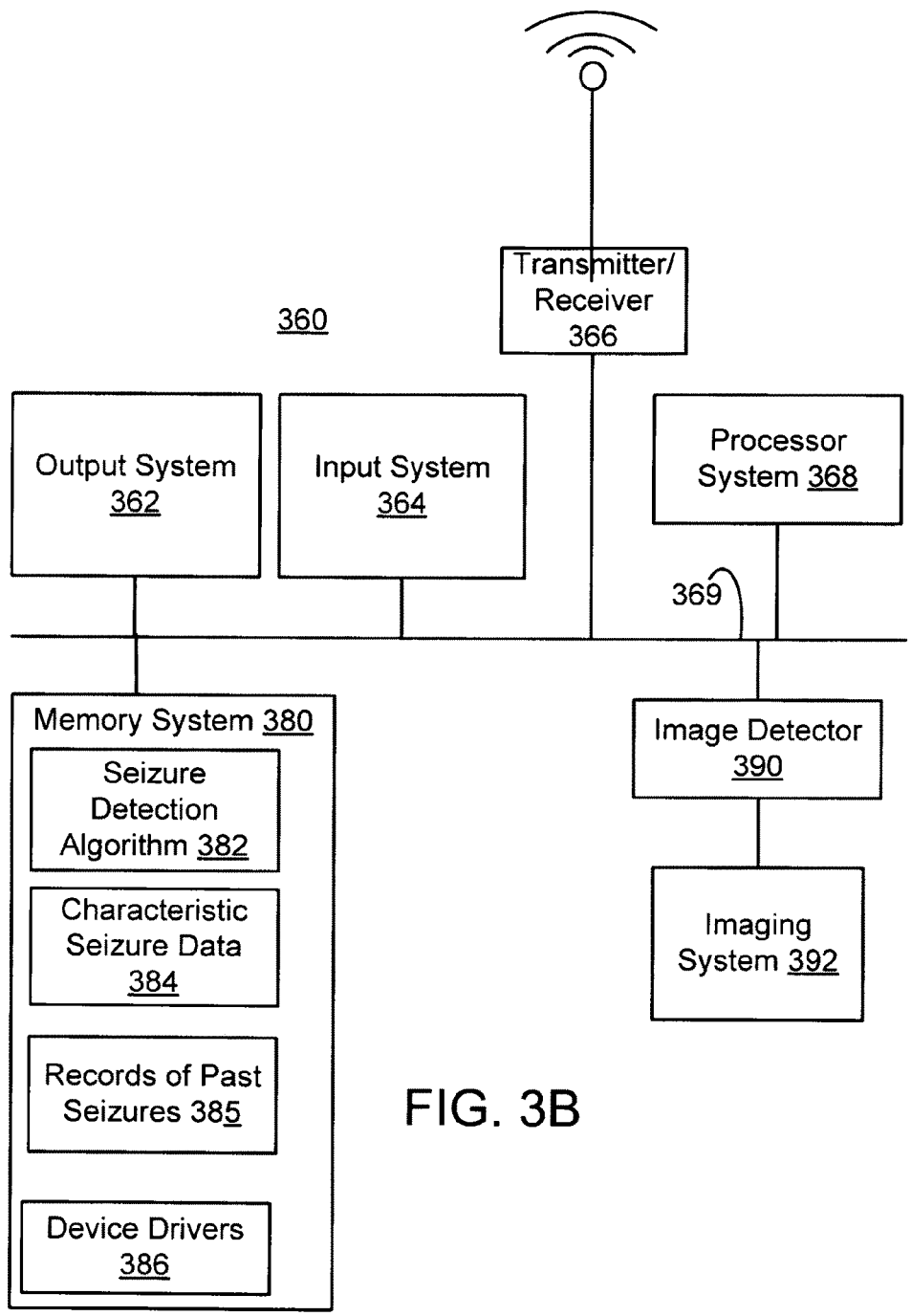
FIG. 3B shows a block diagram of camera 360.

Camera with Processor (FIG. 3B)

FIG. 3B shows a block diagram of camera 360. Camera 360 may include output system 362, input system 364, transmitter/receiver 366, processor system 368, communications system 369, memory 380, which may include seizure detection algorithm 382, characteristic seizure data 384, and device drivers 386. Camera 360 may also include image detector 388 and imaging system 390. In other embodiments, camera 360 may include additional components and/or may not include all of the components listed above.

Output system 362, input system 364, transmitter/receiver 366, processor system 368, communications system 369, memory 380, seizure detection algorithm 382, characteristic seizure data 384, records on past seizures 385, and device drivers 386 have similar descriptions to output system 332, input system 334, transmitter/receiver 336, processor system 338, communications system 339, memory system 340, seizure detection algorithm 342, characteristic seizure data 344, records on past seizures 345, and device drivers 346 of FIG. 3A, respectively. Also, seizure detection algorithm 382, characteristic seizure data 384, records of past seizures 385, device drivers 386 have a similar description as seizure detection algorithm 242, characteristic seizure data 244, records on past seizures 246, and device drivers 248 (FIG. 2B), respectively. However, seizure detection algorithm 382 (FIG. 3B) may be tailored for handling optical data, and characteristic seizure data 384 and records of past seizures 385 (FIG. 3B) may be optical data, whereas seizure detection algorithm 342 (FIG. 3A) may be tailored for accelerometer data and characteristic seizure data 344 and records of past seizures 345 (FIG. 3A) may be accelerometer data. Also device drivers 386 (FIG. 3B) may include device drivers for image detector 388 and/or imaging system 390, whereas device drivers 346 (FIG. 3A) may include device drivers for motion detection hardware 352.

Image detector 388 converts optical images into electrical signals that represent the image and/or motion. For example, image detector 388 may be a charge couple device. Imaging system 390 is the system of lenses and/or other optical components that form the image on image detector 388.

Video Seizure Detection Algorithms

The video detection algorithm is one component of the overall system. Video detection can use one or more of at least 3 types of algorithms:

1: Optical Flow based or feature points based

2: Intelligent Motion based and/or Abnormal behavior based motion analysis

3: Motion vectors (which may be used similar to compression methods)

Figure 4:
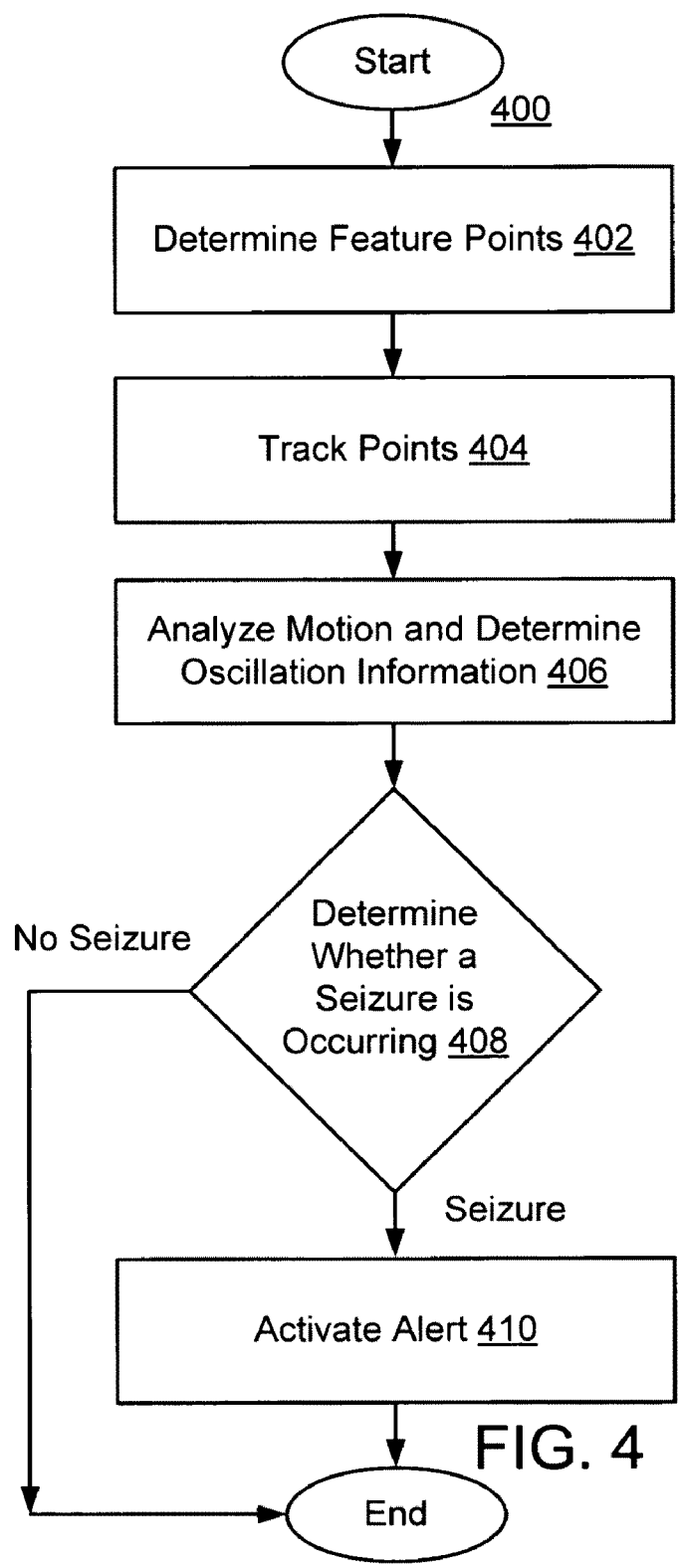
FIG. 4 is a flowchart of an embodiment of a method 400 of detecting a seizure, based on optical flow.

Optical Flow Based Detection (FIG. 4)

FIG. 4 is a flowchart of an embodiment of a method 400 of detecting a seizure, based on optical flow. In step 402, feature points that can be tracked are determined optical flow is detected to track the path of a collection of points. Feature points can also be unique or distinguished points on the person body or cloths. Feature points that can be tracked may be corner points and points which exhibit texture in its local neighborhood, for example. The optical flow technique works by first extracting feature points from the frame that can be tracked reliably. Optical Flow Analysis (or) Feature Point Tracking can be different.

In step 404, the optical flow analysis or feature point tracking algorithm then tracks the motion or flow of points across successive frames. The tracking of points may be done in each successive frame or alternatively, some frames can be skipped, depending upon the nature of motion.

In step 406, the paths of the tracked points are analyzed and/or plotted. For example, the plot of the points the position as a function of time, the velocity, and/or acceleration may be extracted. Information is computed or determined that relate to oscillations of a change of parameter of motion, such as the frequency of the change, the amplitude of change, time over which the change occurs (e.g., the period of oscillation), the area swept out by the body part during the oscillatory movements, and/or path traced by the points being tracked. The frequency of, amplitude of, and area swept by the identified points oscillate indicate the frequency of, amplitude of, and area swept out by the oscillation, respectively. The amplitude may indicate the distance that the points and/or corresponding objects (e.g., body parts) are moving. Area may indicate the area swept out by a moving object. The path may indicate the exact nature and movement patterns of the points and/or corresponding objects. The oscillation analysis as above determines whether a motion is classified that of a seizure. Time over which a particular motion occurs may also be indicative of a seizure. There may be a minimum length of time for the seizure and if the motion does not continue over a length of time longer than the minimum length the motion may be classified as not being part of a seizure.

In step 408 a determination is made based on the oscillation information whether a seizure is occurring. Some or all of the above parameters and/or additional parameters may be used to decide if the movement is a seizure. For example, there may be one or more threshold levels for the frequency, amplitude, and area, and if the motion crosses one or more of the thresholds, it may be determined that there is a seizure. Some thresholds may be proportional ratios or functions of these parameters. In step 410, if it is determined that a seizure is occurring, an alert is activated. In an embodiment, Method 400 is repeated for each set of data until motion detector 110 and/or the processor are turned off.

In an embodiment, each of the steps of method 400 is a distinct step. In another embodiment, although depicted as distinct steps in FIG. 4, step 402-410 may not be distinct steps. In other embodiments, method 400 may not have all of the above steps and/or may have other steps in addition to or instead of those listed above. The steps of method 400 may be performed in another order. Subsets of the steps listed above as part of method 400 may be used to form their own method.

Figure 5:
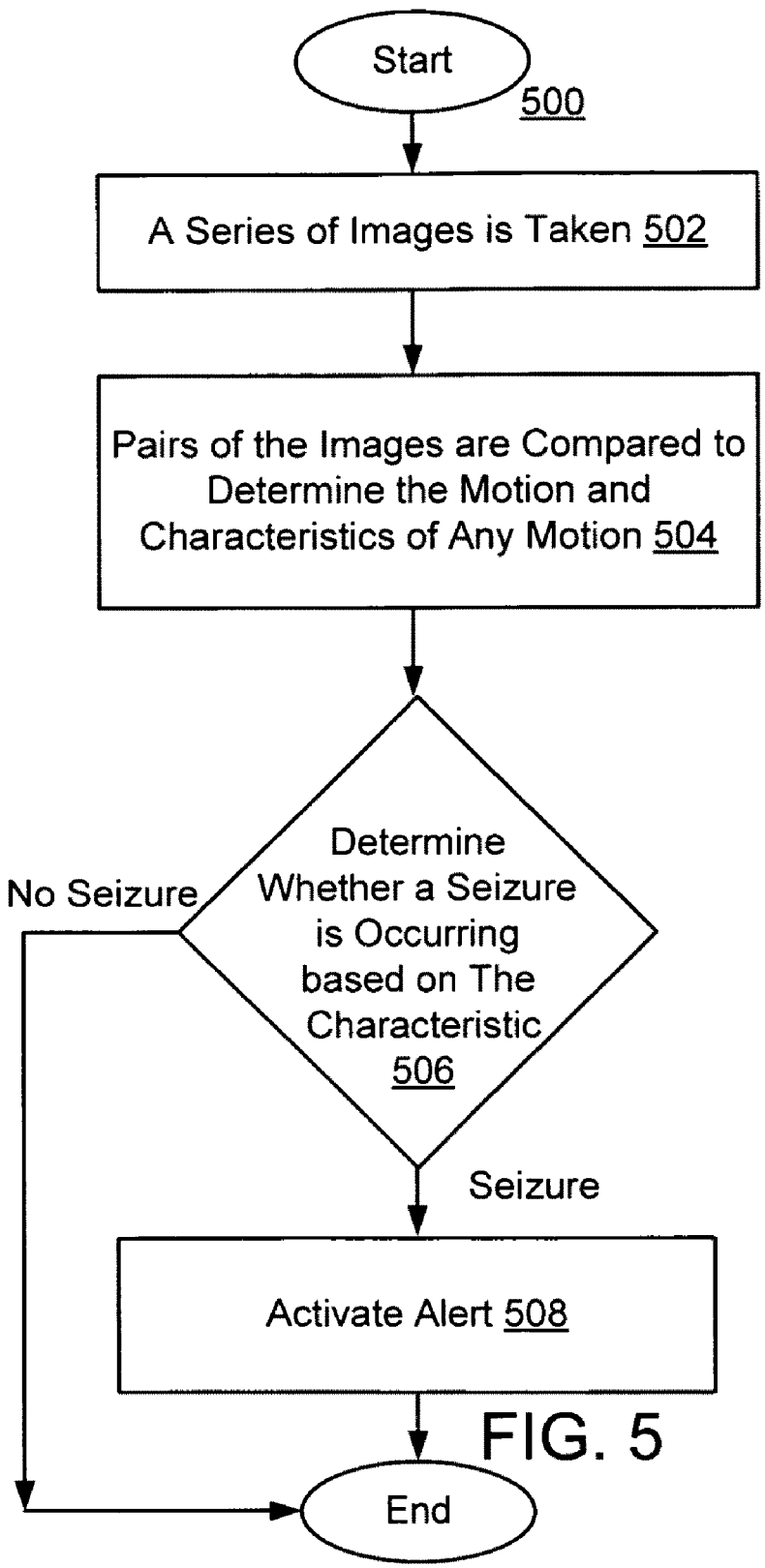
FIG. 5 is a flowchart of an embodiment of a method 500 of detecting a seizure, based on motion analysis.

Intelligent Motion Based and Abnormal Behavior Based a Motion Analysis Algorithm (FIG. 5)

FIG. 5 is a flowchart of an embodiment of a method 500 of detecting a seizure, based on motion analysis. In step 502, pairs of a series of images are taken (e.g., via a video). In step 504, pairs of consecutive images are compared. A video algorithm may analyze a comparison of two images to determine whether there is motion, which may be detected based on pixel changes and image differencing.

In step 506, a determination is made as to whether a seizure has occurred based on the length and duration of the body motion. Optionally, information that is not expected to be relevant to determining whether there was seizure is eliminated using standard techniques. For example, information about lighting and shadows may be eliminated. In the abnormal motion case, the motion signature, duration, length, and/or area are all used to see the abnormal motion behavior. Seizure patterns can are learned and compared.

In step 508, if it is determined that a seizure is occurring, an alert is activated. Returning to step 506, if it is determined that no seizure occurs, method 500 terminates. After termination method 500 may restart on another set of data. In an embodiment, many instances of method 500 may be performed concurrently on different set of data. For example, after a first instance of method 500 starts working on one pair of images, a second instance may start working on the next set of data, which may come from the next available pair of images, before the first instance of method 500 terminates. In an embodiment, method 500 is repeated for each set of data until motion detector 110 and/or the processor are turned off.

In an embodiment, each of the steps of method 500 is a distinct step. In another embodiment, although depicted as distinct steps in FIG. 5, step 502-508 may not be distinct steps. In other embodiments, method 500 may not have all of the above steps and/or may have other steps in addition to or instead of those listed above. The steps of method 500 may be performed in another order. Subsets of the steps listed above as part of method 500 may be used to form their own method.

Figure 6:
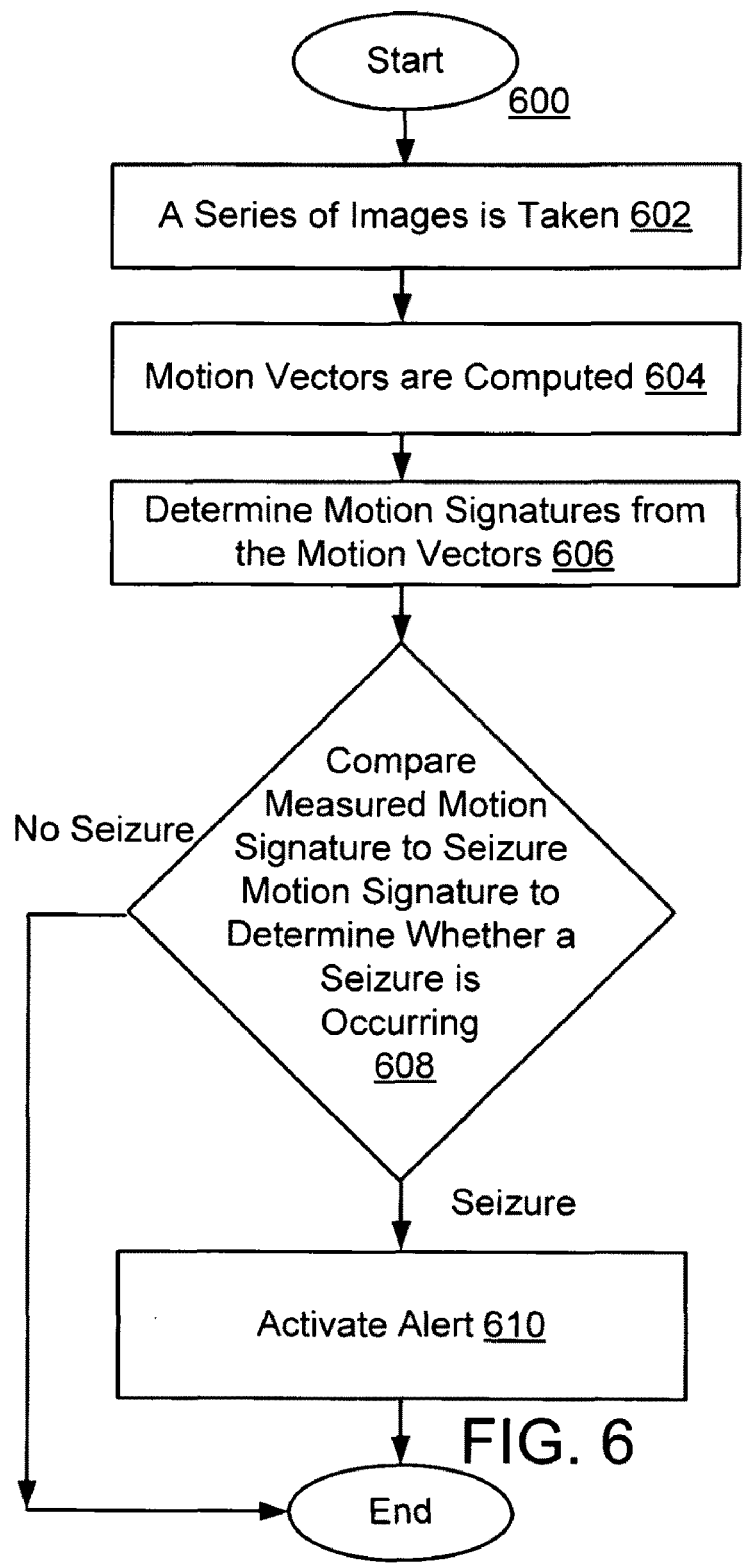
FIG. 6 is a flowchart of an embodiment of a method 600 of detecting a seizure, based on patterns of motion vector patterns.

Motion Vectors Based Algorithm (FIG. 6)

FIG. 6 is a flowchart of an embodiment of a method 600 of detecting a seizure, based on patterns of motion vector patterns. In step 602, a series of images is taken. In step 604, motion vectors are computed. Specifically, two-dimensional vectors that provide offsets from the coordinates in one picture frame to the coordinates in another picture frame are computed. The vectors may be created in a manner similar to the motion vectors created for compression methods or same motion vectors from the compressed video may be used. In an embodiment, the motion vectors are created using IP cameras. In step 606, movement pattern signatures are determined from the motion vectors. In step 608, the movement pattern signatures measured are compared to movement pattern signatures of seizures. A signature may be used for comparison with pattern signatures that are determined to fit a signature that results from a seizure, and if the signature of the pattern measured is close enough to (e.g., within a threshold value of the root mean square of the differences between) the signature of the seizure, an indication that a seizure occurred is generated. In step 610, if it is determined that a seizure is occurring, an alert it activated.

Returning to step 608, if it is determined that no seizure occurs, method 600 terminates. After termination method 600 may restart on another set of data. In an embodiment, many instances of method 600 may be performed concurrently on different set of data. For example, after a first instance of method 600 starts working on one pair of images, a second instance may start working on the next set of data, which may come from the next available pair of images, before the first instance of method 600 terminates. In an embodiment, method 600 is repeated for each set of data until motion detector 110 and/or the processor are turned off.

In an embodiment, each of the steps of method 600 is a distinct step. In another embodiment, although depicted as distinct steps in FIG. 6, step 602-610 may not be distinct steps. In other embodiments, method 600 may not have all of the above steps and/or may have other steps in addition to or instead of those listed above. The steps of method 600 may be performed in another order. Subsets of the steps listed above as part of method 600 may be used to form their own method.

Finally, the method of detecting abnormal or specific motion can also be a hybrid algorithm of all 3 video detection methods (described in FIGS. 4-6). Or the method of detecting abnormal motion can also be an integration of/hybrid between Video and Motion/Accelerometer/Sensor algorithms joined and fused together as final one.

Figure 7:
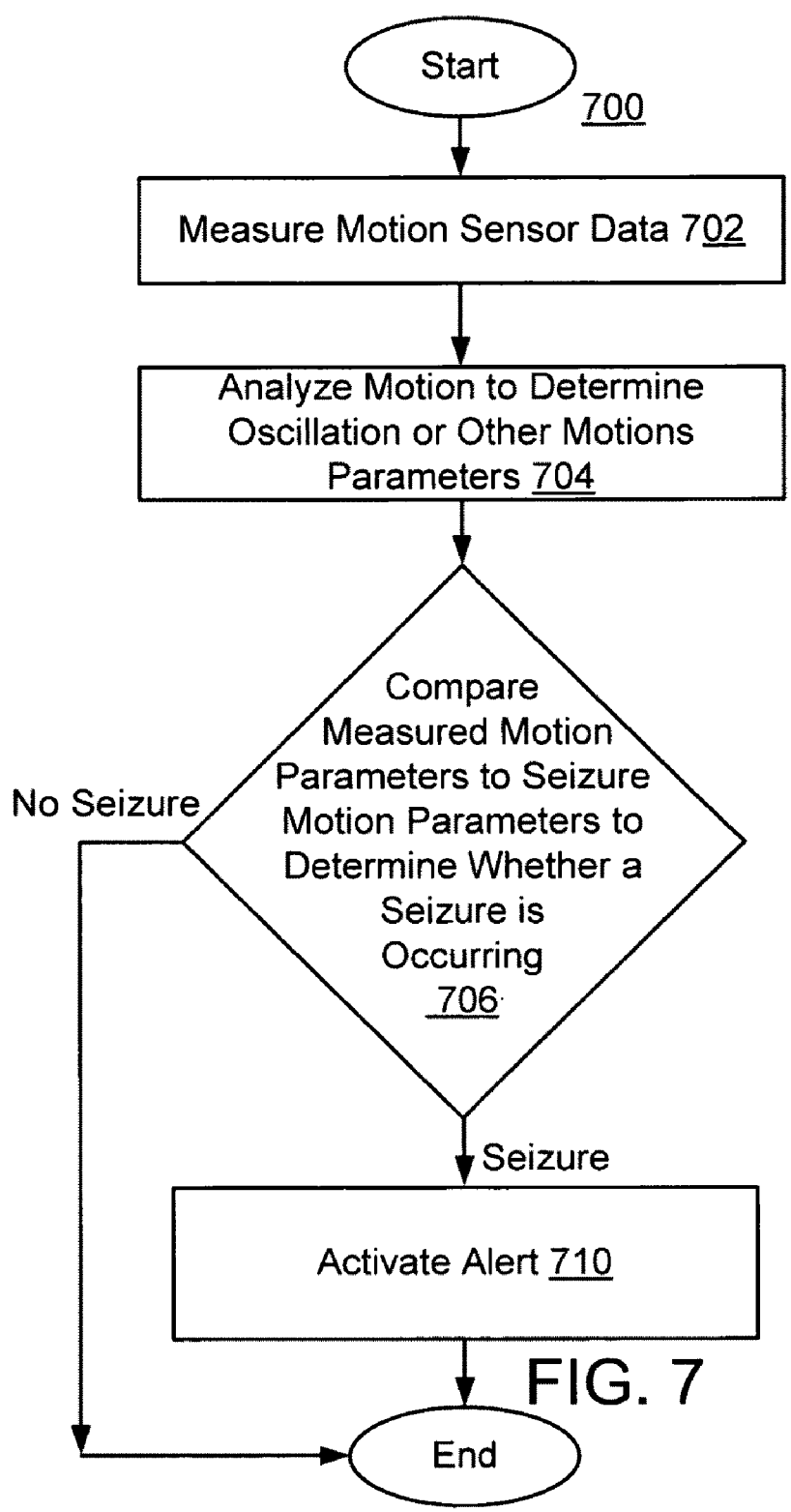
FIG. 7 is a flowchart of an embodiment of a method 700 of detecting seizures by measuring motion, via accelerometers and/or gyro sensors.

Accelerometer Seizure Detection Algorithm (FIG. 7)

FIG. 7 is a flowchart of an embodiment of a method 700 of detecting seizures by measuring motion, via an accelerometer (and/or gyro sensor). An accelerometer sensor provides the acceleration and orientation of the body. The accelerometer is secured to the patient's hand, arm, legs, and/or any other part of body that shakes and has the seizure movements. The following steps are used to detect the seizure from the accelerometer data.

In step 702, the sensor data is obtained by a time based sampling of the motion. For example, 1000 or 10,000 samples per second are collected. In an embodiment, the samples may be an amount of deflection of a cantilever. The data sampling may be in any one or all X, Y, and Z axes. The data per axis may be one dimensional numerical accelerometer data. The motion data may be sampled over time. Hence for the X and Y axes, there will be two data streams. For triple axes data from axes X, Y, and Z, there will be 3 data streams. In an embodiment, the amplitude and frequency are measured as part of the time based data stream. The amplitude, frequency, change of position, and acceleration may be measured from the accelerometer or other motion sensor data. The data may be tracked over time. The data can be tracked in every time interval or specified time internals may be skipped. The time intervals at which the data is sampled define the sampling frequency.

In optional step 704, the path of the data is analyzed or plotted. Data such as points, position, acceleration, velocity, and/or speed are extracted. If the points, positions, velocities, and acceleration were already determined as part of step 702, step 704 may be skipped.

In step 706, an oscillation analysis is performed, as described above, may be used to determine whether a seizure takes place. The frequency, amplitude, time, and/or path of the oscillation may be determined. Frequency may determine how frequently the sensor and objects oscillate. The amplitude may indicate the amount of distance that the objects move. The path may indicate the exact nature and movement patterns of the objects. The frequency, amplitude, and/or path may be used to analyze oscillations and decide if the movement is a seizure.

Returning to step 708, if it is determined that no seizure occurs, method 700 terminates. After termination method 700 may restart on another set of data. In an embodiment, many instances of method 700 may be performed concurrently on different set of data. For example, after a first instance of method 700 starts working on one pair of images, a second instance may start working on the next set of data, which may come from the next available pair of images, before the first instance of method 700 terminates. In an embodiment, method 700 is repeated for each set of data until motion detector 110 and/or the processor are turned off.

The detection algorithm can use any of one or more of the following mathematical methods. In one embodiment, the peak and amplitude of the oscillation are checked, and compared to thresholds value of the peaks and amplitude. In an embodiment, if the peak and/or amplitude are greater than the threshold, then a determination is made that the oscillation is associated with a seizure. An absolute and/or relative threshold may be used to find abnormalities, which may indicate a seizure.

In another embodiment, a search is made for repeated peaks and valleys in the one dimensional sensor data (for X, Y, and/or Z). This technology uses the motion vector patterns based algorithm. Repeated and distinguished peaks and valleys may indicate seizures.

In another embodiment, a search is made for duplicate peaks on other axes. In other words, one axis may have stronger peaks while the others may have weaker peaks. In some cases all axes can be stronger or weaker. However, neighboring axes can provide a valuable confirmation when the peaks on one axis have corresponding peaks on another axis.

In another embodiment, software and/or hardware neural networks or other learning methods may determine abnormal patterns to detect seizures. In another embodiment, exact template patterns or signal patterns can be used to match other signal patterns. A prior known seizure pattern can be used to compare the signal pattern with the known template and if the pattern detected matches the known seizure pattern within a given tolerance, then it is expected that a seizure occurred. These neural networks or other machines using other learning methods, can be either supervised or unsupervised learning.

In another embodiment, the position may be analyzed by determining the first derivative and the second derivative of a signal that is indicative of the position as a function of time. The first and second derivative of the position signal may be monitored to determine whether the first and second derivative are within a range that is considered to be an average and/or normal change of position (an average and normal first derivative dx/dt and an average and normal rate of change of position, which is the $2^{nd}$ derivative, $d^2x/dt^2$). When the first and/or second derivative are abnormal, or beyond a threshold then an indication is generated that a seizure may have been detected. Additionally, if the periodic changes of the first and second derivative are outside of a certain range, it may be an indication that a seizure has occurred. Periodic changes in the second derivate are the third derivates, which are the impulses, which may be used to characterize jerky motion. Similarly, if the third derivative (or another derivative) is beyond a threshold or is not within a range that is considered normal, an indication that a seizure occurred may be generated. Additionally, if the pattern of times at which the third derivatives rise above a certain threshold matches that of a known pattern for a seizure and/or occur at a frequency that is expected to be indicative of a seizure, an indication that a seizure has occurred in generated.

In another embodiment, statistical learning or probabilistic methods are used. Machine learning strategies based on Bayesian Network (Bayes net) and HMM (Hidden Markov Models) and other statistical learning or probabilistic methods can be used for detection of seizure.

In another embodiment, local, regional, and/or global features are detected. The features may be a collection of data taken from a neighborhood of a signal with temporal information. Local features are characteristics of signal and/or data in a small region of the data. Local features are a function of time (e.g., the features of a plot of the signal as a function of time), regional features covers more time, and global features are an average or a collection of local/regional features over longer time. Both local and global features can be a combination of both shape and time/temporal based. The local and global features are detected and compared to known local, regional and global features that are expected to characterize seizure features to determine whether a seizure has occurred. If the local, regional and global features that are associated with a seizure occur, then a signal is generated indicating that seizure has occurred.

Individual Person's Seizure Signature

In one mode or embodiment, a person's seizure data or motion signature may be measured as a seizure occurs. "Seizure detection" parameters (frequency, amplitude, patterns) can be customized as a "seizure signature" for each patient. This signature can be adjusted and configured for each patient if required for higher accuracy, as opposed to standard factory defaults.

Instead of a fixed seizure signature, the person's signature may be determined over time. Then the detection algorithm will adapt and fine-tune the seizure detection parameters based on the individuals' signature patterns—such as frequency, amplitude, time, area, path, and/or other parameters).

Figure 8:
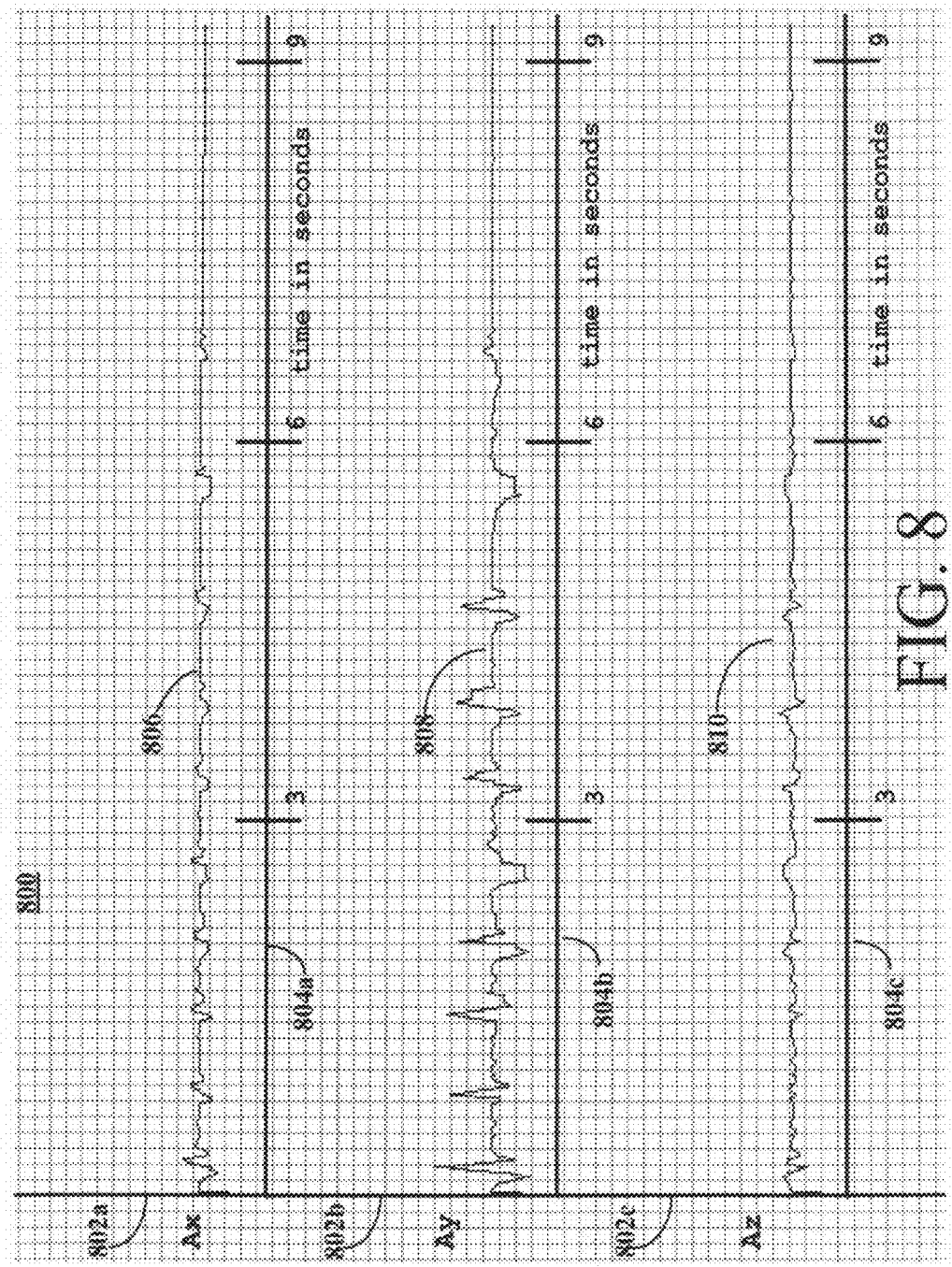
FIG. 8 shows a graph 800 of three orthogonal components of acceleration of an arm.

FIG. 8 shows a graph 800 of three orthogonal components of acceleration of an arm. Graph Graph 800 includes a vertical axis 802a-c, horizontal axis 804a-c, and plots 806, 808, and 810. Horizontal axis 802a-c is the time axis, and vertical axes 804a-c are the amplitude axes. Plots 806, 808, and 810 are plots of each of the three components of acceleration labeled X, Y, and Z, which are measured in a reference frame that is stationary with respect to the wrist. Graph 800 shows 9 peaks with about 5 second. The threshold for the number of peaks within a window of 6 seconds should be 9 peaks or less. The magnitude for the peaks of the y component of acceleration is 6 cm/sec$^2$, and the threshold for a single component of acceleration should be less than 6 cm/sec$^2$.

Figure 9:
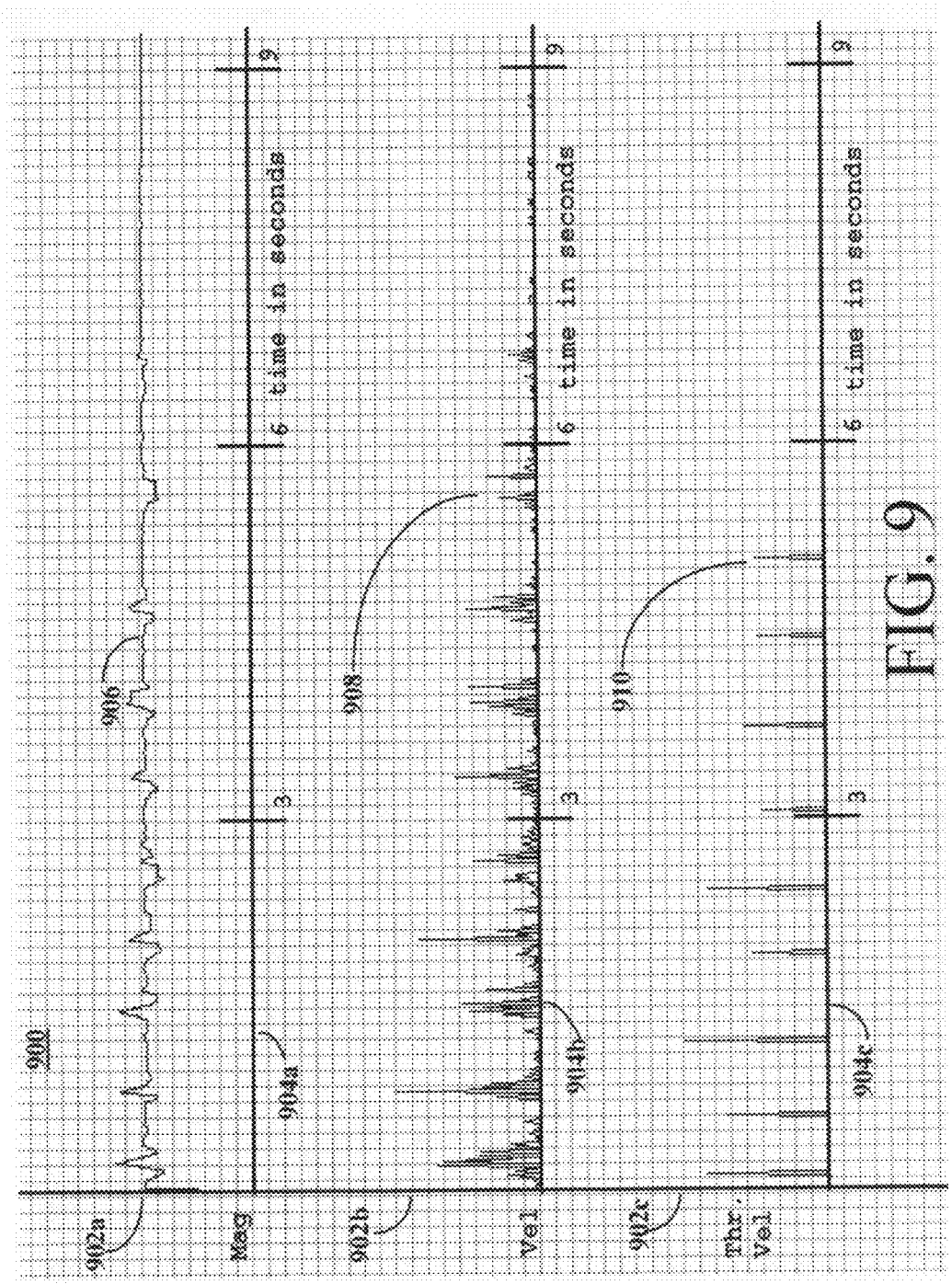
FIG. 9 shows a graph 900 of two parameters of motion.
Figure 10:
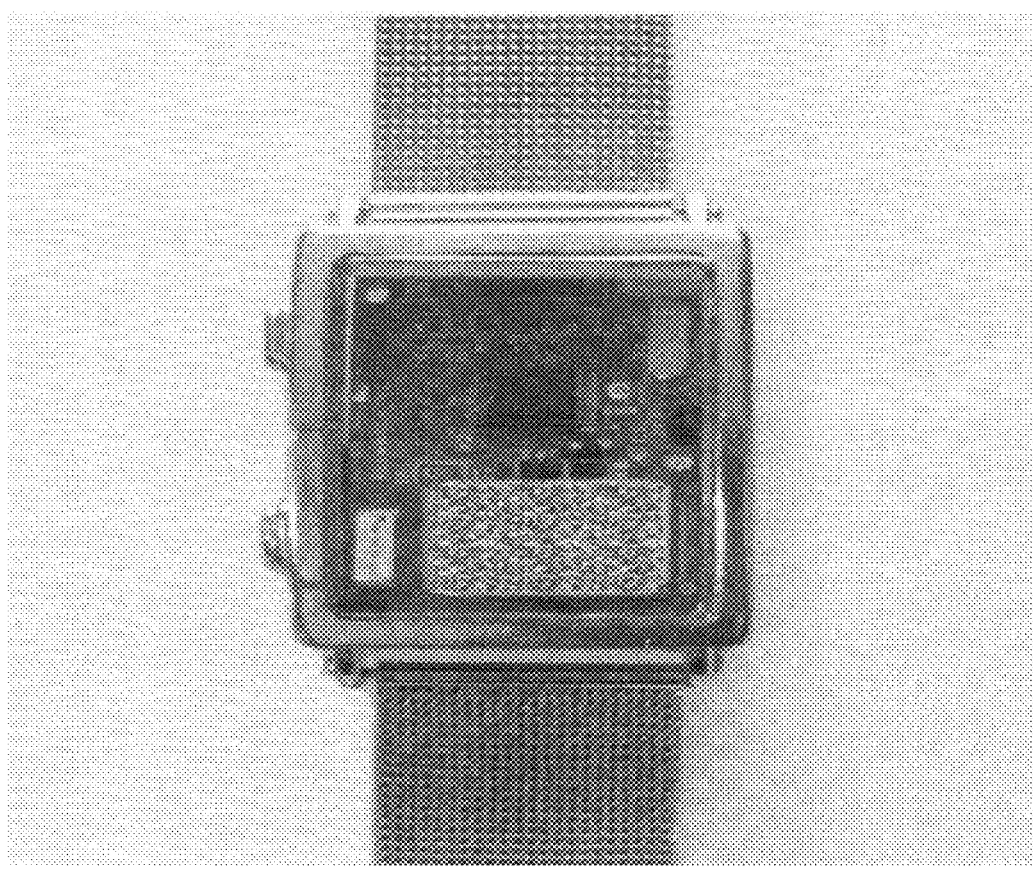
FIG. 10 shows an embodiment of a seizure detection, analyzing, and monitoring device.

FIG. 9 shows a graph 900 of two parameters of motion. Graph 900 includes a vertical axis 902, horizontal axis 904, and plots 906, 908, and 910. Horizontal axis 902 is the time axis, and vertical axes 904a-c is the amplitude axis. Plot 906 plots the magnitude of the acceleration vector. Plot 908 plots the first derivative of the magnitude of acceleration. Plot 910 is also a plot of the are plots of the first derivative of the magnitude of acceleration. However, peaks that were below a predetermined threshold were removed. If the number of peaks within a specified window of time are greater than predetermined number, it is an indication of a seizure.

In FIGS. 8 and 9 the units for acceleration are m/sec$^2$ and the units for impulse or jerk are m/sec$^3$. In an embodiment, for at least some patients the threshold for the magnitude of acceleration may be about 7 m/sec$^2$. The threshold for a "jerk" or impulse, may be about a number less than 4 m/sec$^3$ e.g., 3 m/sec$^3$, 3.5 m/sec$^3$, or 3.8 m/sec$^3$. The threshold for the frequency of peaks in acceleration may 3/(3 seconds) (e.g., 1 Hz). The number peaks in a window of 3 seconds there should be at least 3 peaks. The threshold for the number of peaks in the impulse should be at least 3, and within a window of about 3 seconds there should be at least 3 peaks in the impulse/jerk. In other embodiments, the units and the values for the thresholds above may be proportional to those given above.

Extensions and Alternatives

Each embodiment disclosed herein may be used or otherwise combined with any of the other embodiments disclosed. Any element of any embodiment may be used in any embodiment.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

The invention claimed is:

1. A body-worn portable device comprising:
a strap for strapping the body-worn portable device onto a person;
an input system for inputting detections parameters for a specific type of abnormal motion;
an accelerometer or gyro sensor for measuring motion data;
a memory storing settings for detecting the specific type of abnormal motion including at least characteristics of the specific type of abnormal motion;
an algorithm for analyzing the motion data measured, comparing the characteristics of the specific type of abnormal motion to the motion data measured, and determining whether to send an alert based on the comparing;
a processor that implements the algorithm and generates an indication that the abnormal motion may have occurred based on the algorithm;
a housing for enclosing the memory and the processor; and
a display being attached to the housing in a manner in which the settings for the specific type of abnormal motion or a status may be viewed,
the input system being attached to the housing in a manner in which settings for the specific type of abnormal motion may be entered by the person, and
wherein the specific type of abnormal motion includes a seizure.

2. The body-worn portable device of claim 1, the memory storing data indicating events that occurred and alerts that were sent.

3. The body-worn portable device of claim 1, the input system having at least
a first portion, which when manually activated, causes an alert to be sent; and
a second portion, which when manually activated, causes a sending of an alert to be cancelled.

4. The body-worn portable device of claim 1
the strap straps the body-worn portable device onto a wrist of the body when worn on the body.

5. A body-worn portable device comprising:
a strap for strapping the body-worn portable device onto a person;
an input system for inputting detections parameters for a specific type of abnormal motion;
an accelerometer or gyro sensor for measuring motion data;
a memory storing settings for detecting the specific type of abnormal motion including at least characteristics of the specific type of abnormal motion;
an algorithm for analyzing the motion data measured, comparing the characteristics of the specific type of abnormal motion to the motion data measured, and determining whether to send an alert based on the comparing;
a processor that implements the algorithm and generates an indication that the abnormal motion may have occurred based on the algorithm;
a housing for enclosing the memory and the processor;
a display being attached to the housing in a manner in which the settings for the specific type of abnormal motion or a status may be viewed,
the input system being attached to the housing in a manner in which settings for the specific type of abnormal motion may be entered by the person;
a clock mounted within the housing; and
a display for displaying a time of day;
the clock being for determining a time of day to display on the display;
the input system having a portion via which the time can be changed and can be adjusted, and
wherein the specific type of abnormal motion includes a seizure.

6. A body-worn portable device comprising:
a strap for strapping the body-worn portable device onto a person;
an input system for inputting detections parameters for a specific type of abnormal motion;
an accelerometer or gyro sensor for measuring motion data;
a memory storing settings for detecting the specific type of abnormal motion including at least characteristics of the specific type of abnormal motion;
an algorithm for analyzing the motion data measured, comparing the characteristics of the specific type of abnormal motion to the motion data measured, and determining whether to send an alert based on the comparing;
a processor that implements the algorithm and generates an indication that the abnormal motion may have occurred based on the algorithm;
a housing for enclosing the memory and the processor;
a display being attached to the housing in a manner in which the settings for the specific type of abnormal motion or a status may be viewed,
the input system being attached to the housing in a manner in which settings for the specific type of abnormal motion may be entered by the person;
the characteristics of the specific type of motion including a first threshold and a second threshold;
the algorithm stored in the memory including at least one or more instructions for computing a time derivative of acceleration; determining whether one or more peaks of a time derivative of the accelerations is above the first threshold; determining a count of how many peaks occur within a window of time that are higher than the first threshold; determining whether the count is greater than the second threshold; and if the count is greater than the second threshold, generating an indication that the specific type of motion occurred, and
wherein the specific type of abnormal motion includes a seizure.

7. The body worn portable device of claim 6, the algorithm stored on memory further including at least receiving a user chosen value, via the input system, for the first threshold.

8. The wrist or body worn portable device of claim 7, the algorithm stored on memory further including at least receiving a user chosen value, via the input system, for the second threshold.

9. The body-worn portable device of claim 6, the characteristics of the specific type of motion including a third threshold and a fourth threshold;
   the count being a first count;
   the algorithm stored in the memory including at least one or more instructions for determining whether the one or more peaks of the time derivative of the acceleration is above the third threshold;
      determining a second count of how many peaks occur within a window of time that are higher than the third threshold; and
      determining whether the second count is greater than the fourth threshold; and
      if the second count is greater than the fourth threshold, storing motion activity in the memory.

10. A system comprising:
   a motion detector measuring motion data associated with a person;
   a memory having stored thereon an algorithm including at least analyzing motion data, determining whether the motion data indicates that a specific type of motion has occurred based on the analyzing, and if it is determined that the specific type of motion has occurred, generating an indication that the specific type of motion occurred, based on the determining; and
   a processor for implementing the algorithm to determine whether motion data collected by the motion detector corresponds to the specific type of motion;
   the specific type of motion being an abnormal motion including a seizure.

11. The system of claim 10, the indication that the specific type of motion occurred being an alert, and the algorithm also including sending the alert.

12. The system of claim 10 where the specific type of motion includes at least a shake having at least a sudden to and fro movement.

13. The system of claim 10, the motion detector including at least a plurality of cameras, and the motion data being images of the person.

14. The system of claim 13, the algorithm including a method of determining an optical flow of images, and the analyzing of the motion data including analyzing the optical flow.

15. The system of claim 13, the algorithm including a method of determining motion vectors from images, and the analyzing of the motion data including analyzing the motion vectors.

16. The system of claim 10, wherein the motion detector includes at least an accelerometer or gyro sensor, and the motion data being output of the accelerometer or gyro sensor.

17. The system of claim 10, further comprising location determination hardware for determining a location of the person.

18. The system of claim 10, further comprising global positioning system hardware and global positioning system software for determining a location of the person.

19. The system of claim 10, the motion data including at least a threshold value for a frequency of oscillation of a body part;
   the analyzing including at least comparing a value characterizing the motion to the threshold; and
   the determining including at least determining whether the value crossed the threshold based on the comparing to determine whether the specific type of motion has occurred.

20. The system of claim 10, the motion data including one or more motion patterns characterizing a specific type of motion;
   the analyzing including at least comparing a motion pattern derived from the data collected during the collecting to the one or more motion patterns characterizing a specific type of abnormal motion; and
   the determining including at least determining whether the motion pattern derived matches within a predetermined tolerance of one of the one or more motion patterns characterizing the specific type of abnormal motion.

21. The system of claim 10, the analyzing including at least determining oscillatory motion; and
   determining one or more parameters characterizing the oscillatory motion.

22. The system of claim 21, the motion data including at least a frequency of oscillation;
   the determining whether the motion data indicates that a specific type of motion has occurred including at least comparing the frequency of oscillation to a predetermined threshold; and
   the determining one or more parameters characterizing the oscillatory motion including at least determining whether the frequency of oscillation is higher than the predetermined threshold
   the algorithm further including at least activating of an alert if the frequency of oscillation is higher than the predetermined threshold.

23. The system of claim 10, the algorithm also including at least receiving training data related to several events, each event being known to include at least portion of a specific type of abnormal motion;
   the analyzing including at least determining whether an unknown event is a specific type of abnormal motion based on the training data.

24. The system of claim 23, the training data also including at least one event known not to include a specific type of abnormal motion.

25. The system of claim 10, the analyzing including at least determining how many peaks in a magnitude of acceleration occur during a period of time;
   the determining whether the motion indicates a specific type of motion includes at least determining if the number of peaks is greater than a threshold.

26. The system of claim 10, the analyzing including at least determining how many peaks in at least one component of acceleration occur during a period of time;
   the determining whether the motion indicates a specific type of motion includes at least if the number of peaks is greater than a threshold.

27. The system of claim 10, the analyzing including at least determining how many jerks occur during a period of time;
   the determining of whether the motion indicates a specific type of motion includes at least determining if the number of jerks is greater than a threshold, sending an alert.

28. The system of claim 27, each jerk of the jerks being an absolute value of a numerical estimate of a first derivative of a magnitude of acceleration.

29. The system of claim 10, the analyzing including at least computing a second derivative of acceleration of the one or more parts of the body during a specified window;
   the determining of whether the motion indicates a specific type of motion includes at least determining how many second derivative within the specified window have crossed a threshold indicative of a specific type of motion.

30. The system of claim 10, the analyzing including at least representing the motion as a sum of basis functions multiplied by coefficients;
  the determining of whether the motion indicates a specific type of motion includes at least determining if a magnitude of the one or more coefficients crosses a predetermined threshold that is known to be an indication of a specific type of motion.

31. The system of claim 10, the algorithm including rules for determining a specific type of motion.

32. The system of claim 10, the algorithm including a statistical model of data associated with a specific type of motion for determining a specific type of motion.

33. The system of claim 10, further comprising a neural network for determining whether data is indicative of a specific type of motion.

34. The system of claim 10, the algorithm including at least rules for determining a specific type of motion;
  a statistical model of data associated with a specific type of motion for determining a specific type of motion; and
  a training routine for learning behaviors associated with a specific type of motion; and
  the system further comprising a neural network for determining whether data is indicative of a specific type of motion.

35. The system of claim 10, the indication that the specific type of motion occurred is an alert, the system further comprising:
  a transmitter that transmits
    the alert to a remote location associated with a concerned party to protect the health of an individual associated with specific type of motion, which is abnormal, the alert being in response to signals received from the processor resulting from the processor determining that a specific type of motion occurred based on the processor implementing the algorithm.

* * * * *